(12) United States Patent
Park et al.

(10) Patent No.: US 8,369,482 B2
(45) Date of Patent: Feb. 5, 2013

(54) ELECTRODE INSPECTION DEVICE FOR BATTERY AND METHOD OF THE SAME

(75) Inventors: Hee Chan Park, Daejeon (KR); Jin Gyu Kim, Daejeon (KR); Ik Sung Yoon, Daejeon (KR); Sang Bum Kim, Seoul (KR)

(73) Assignee: SK Innovation Co., Ltd., Jongro-gu, Seoul (KR)

( * ) Notice: Subject to any disclaimer, the term of this patent is extended or adjusted under 35 U.S.C. 154(b) by 259 days.

(21) Appl. No.: 12/910,078

(22) Filed: Oct. 22, 2010

(65) Prior Publication Data
US 2011/0096900 A1 Apr. 28, 2011

(30) Foreign Application Priority Data

Oct. 26, 2009 (KR) .................. 10-2009-0101977
Jul. 30, 2010 (KR) .................. 10-2010-0073773

(51) Int. Cl.
*G01B 15/06* (2006.01)
(52) U.S. Cl. .................................................. 378/58

(58) Field of Classification Search .............. 378/51, 378/54, 55, 57, 58
See application file for complete search history.

(56) References Cited

FOREIGN PATENT DOCUMENTS
JP 2011-039014 * 2/2011

* cited by examiner

*Primary Examiner* — Jurie Yun
(74) *Attorney, Agent, or Firm* — The Webb Law Firm

(57) ABSTRACT

The present invention relates to an apparatus and method for inspecting the electrodes of a battery, which inspects the arrangement state of anodes and cathodes in the battery in a non-destructive manner (using X-rays). The apparatus radiates X-ray beams onto a battery in which a plurality of plate-shaped anodes and a plurality of plate-shaped cathodes are alternately stacked and inspects an arrangement state of the anodes and the cathodes. The apparatus includes a first X-ray source part for radiating a first X-ray beam onto the battery. A first detector detects the first X-ray beam having transmitted through the battery. A control unit receives an image of the battery output from the first detector, calculates a step difference between each anode and each cathode, and then inspects an arrangement state of the anode and the cathode.

7 Claims, 14 Drawing Sheets

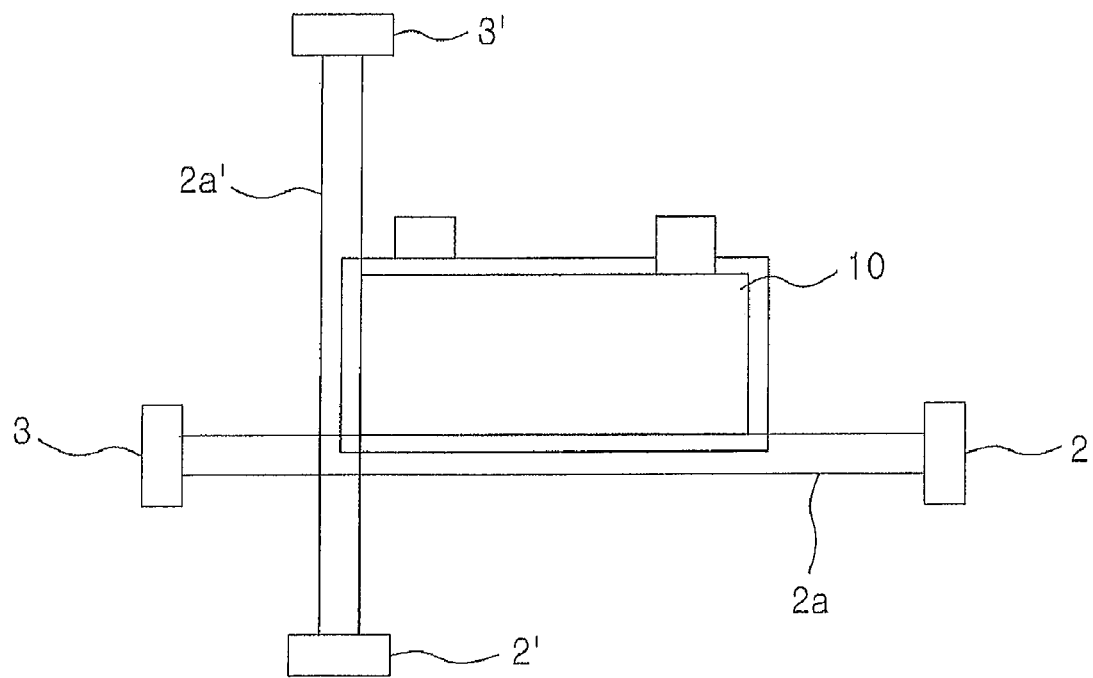

ELECTRODE INSPECTION DEVICE FOR BATTERY AND METHOD OF THE SAME

BACKGROUND OF THE INVENTION

1. Field of the Invention

The present invention relates, in general, to an apparatus and method for inspecting the electrodes of a battery, and, more particularly, to an apparatus and method for inspecting the electrodes of a battery, which inspects the arrangement state of anodes and cathodes in the battery in a non-destructive manner (using X-rays).

2. Description of the Related Art

Recently, the development of mobile devices such as mobile phones or notebook computers and the practicalization of hybrid vehicles have increased the need for secondary batteries such as lithium-ion batteries or nickel-hydrogen batteries. Accordingly, explosions attributable to the shorts or the heating of secondary batteries have become a hot issue, and thus the importance of inspecting batteries to provide safe and reliable batteries has currently increased.

Referring to FIG. 1, a battery 10 may include a hollow casing 13 having the shape of a rectangular parallelepiped, and anodes 11 and cathodes 12 installed in the casing 13. The anodes 11 and the cathodes 12 may be formed in such a way that a plurality of plate-shaped anodes 11 and a plurality of plate-shaped cathodes 12 are paired, and the respective pairs are stacked in the casing 13. The anodes 11 and the cathodes 12 may be alternately stacked.

It is feared that if the anodes 11 are formed to extend to be longer than the cathodes 12 when the anodes 11 and the cathodes 12 are stacked, lithium which is one of materials constituting the battery 10 is separated from the longer anodes at the time that the battery 10 is used, and thus the battery 10 may be shorted or ignition attributable to heat may occur. Due to this, it is very important to form the cross-sectional areas of the anodes 11 so that they are smaller than those of the cathodes 12. Further, it is very important to stack the anodes 11 and the cathodes 12 in a stepped manner so that the peripheral sides of the anodes 11 do not deviate from the peripheral sides of the cathodes 12. In order to inspect the state of the arrangement of the anodes 11 and the cathodes 12, that is, the step difference, X-ray fluoroscopy which is a non-destructive method has been used.

As shown in FIG. 2, a conventional apparatus for inspecting a battery employs a scheme for determining images detected by a first detector 3 by radiating a first X-ray beam 2a from a first X-ray source (source part) 2 along the first and second longitudinal sides of the battery 10 and images detected by a second detector 3' by radiating a second X-ray beam 2a' from a second X-ray source (source part) 2' along the first and second lateral sides of the battery 10, and then inspecting the arrangement state of the electrodes of the battery 10.

The above-described apparatus for inspecting the battery uses a method of conducting inspection by transmitting X-rays along the lateral and longitudinal directions of the battery. Accordingly, a problem arises in that if the length for which the X-rays pass through the battery exceeds a predetermined length, accurate images cannot be obtained due to the scattering of frequencies, and the reliability of inspection is deteriorated.

SUMMARY OF THE INVENTION

Accordingly, the present invention has been made keeping in mind the above problems occurring in the prior art, and an object of the present invention is to provide an apparatus and method for inspecting the electrodes of a battery, which calculates the arrangement state of the electrodes by transmitting X-rays through the corners of the battery, so that the distance X-rays are transmitted is shortened, thus improving the reliability of inspections.

In order to accomplish the above object, the present invention provides an apparatus for inspecting electrodes of a battery, the apparatus radiating X-ray beams onto a battery in which a plurality of plate-shaped anodes and a plurality of plate-shaped cathodes are alternately stacked and inspecting an arrangement state of the anodes and the cathodes, the apparatus including a first X-ray source part for radiating a first X-ray beam onto the battery; a first detector for detecting the first X-ray beam having transmitted through the battery; and a control unit for receiving an image of the battery output from the first detector, calculating a step difference between each anode and each cathode, and then inspecting an arrangement state of the anode and the cathode, wherein the first X-ray source part radiates the first X-ray beam in a direction parallel with a stacked surface of the anode and the cathode of the battery so that the first X-ray beam is radiated at a predetermined angle of inclination in a direction horizontal to a ground surface.

Preferably, the apparatus may further include an inspection plate configured to allow the battery to be placed thereon and to be rotated in a horizontal direction.

Preferably, the apparatus may further include a second X-ray source part spaced apart from the first X-ray source part by a predetermined distance and configured to radiate a second X-ray beam onto the battery; and a second detector for detecting the second X-ray beam having transmitted through the battery, wherein both corners of a first side or a second side of the stacked surface of the anode and the cathode of the battery are simultaneously captured by the first X-ray source part and the second X-ray source part, and an image of the battery output from the second detector enables a step difference between the anode and the cathode to be calculated by the control unit, thus enabling the arrangement state of the anode and the cathode to be inspected.

Further, the present invention provides a method of inspecting electrodes of a battery using the apparatus for inspecting the electrodes of the battery, wherein the first X-ray source part rotates the battery by rotating the inspection plate, and sequentially radiates the X-ray beams onto both corners (A and B) of a first side and both corners (C and D) of a second side of the stacked surface of the anode and the cathode of the battery, four times.

Furthermore, the present invention provides a method of inspecting electrodes of a battery using the apparatus for inspecting the electrodes of the battery, wherein the first X-ray source part radiates the X-ray beam onto a first corner (A) of the first side of the stacked surface of the anode and the cathode of the battery while the second X-ray source part radiates the X-ray beam onto a second corner (B) of the first side of the stacked surface of the anode and the cathode of the battery, the inspection plate is rotated at an angle of 180 degrees, and then the first X-ray source part radiates the X-ray beam onto a second corner (C) of the second side of the stacked surface of the anode and the cathode of the battery while the second X-ray source part radiates the X-ray beam onto a first corner (D) of the second side of the stacked surface of the anode and the cathode of the battery.

In addition, the present invention provides a method of inspecting electrodes of a battery using the apparatus for inspecting the electrodes of the battery, wherein the first X-ray source part radiates the X-ray beam onto a first corner (A) of the first side of the stacked surface of the anode and the cathode of the battery while the second X-ray source part radiates the X-ray beam onto a second corner (B) of the first side of the stacked surface of the anode and the cathode of the battery, the inspection plate is rotated at an angle of less than 90 degrees to rotate the battery at a predetermined angle, and then the first X-ray source part radiates the X-ray beam onto a first corner (A') of the first side of the stacked surface, an angle of which has changed while the second X-ray source part radiates the X-ray beam onto a second corner (B') of the first side of the stacked surface, an angle of which has changed.

Preferably, if a distance between an anode corner (dy1) and a cathode corner (dx1) at the first corner (A) of the first side of the battery, which have been measured by the first X-ray source part is defined as d1; an angle formed between a lateral side of the cathode and the first X-ray source part when $d_1$ is measured is defined as θ1; a distance between an anode corner (dy1') and a cathode corner (dx1') at the first corner (A') of the first side of the battery, which have been measured by the first X-ray source part and have changed due to a change in the angle of the battery after the battery had been rotated at the predetermined angle, is defined as d1'; and an angle formed between the lateral side of the cathode and the first X-ray source part when the distance (d1') is measured is defined as θ2, a distance (X1) between a lateral side of the anode and the lateral side of the cathode at the first corner (A) of the first side of the battery and a distance (Y1) between a longitudinal side of the anode and a longitudinal side of the cathode at the first corner (A) of the first side of the battery are calculated by the following equations:

$$X1 = \frac{1}{\tan(\theta 2) - \tan(\theta 1)} \left( \frac{d1'}{\cos(\theta 2)} - \frac{d1}{\cos(\theta 1)} \right)$$

$$Y1 = \frac{-\tan(\theta 1)}{\tan(\theta 2) - \tan(\theta 1)} \left( \frac{d1'}{\cos(\theta 2)} - \frac{d1}{\cos(\theta 1)} \right) + \frac{d1}{\cos(\theta 1)}$$

BRIEF DESCRIPTION OF THE DRAWINGS

The above and other objects, features and advantages of the present invention will be more clearly understood from the following detailed description taken in conjunction with the accompanying drawings, in which:

FIG. 2 is a conceptual view showing a conventional apparatus for inspecting the electrodes of a battery;

DESCRIPTION OF THE PREFERRED EMBODIMENTS

Figure 1A:
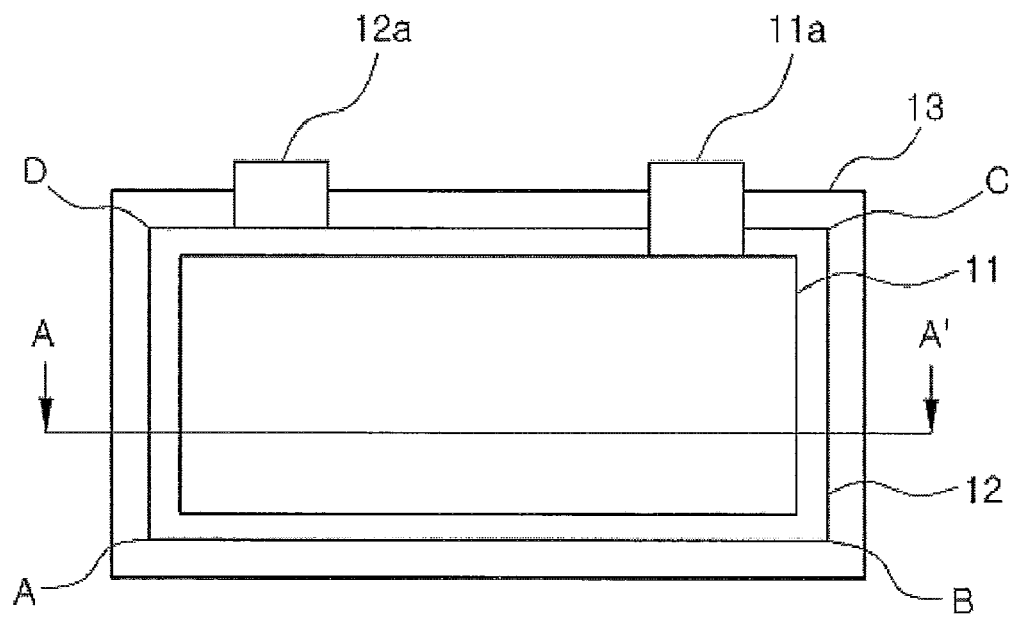
FIG. 1A is a front view of a battery.

Hereinafter, embodiments of the present invention will be described in detail with reference to the attached drawings.

Reference now should be made to the drawings, in which the same reference numerals are used throughout the different drawings to designate the same or similar components.

Figure 1B:
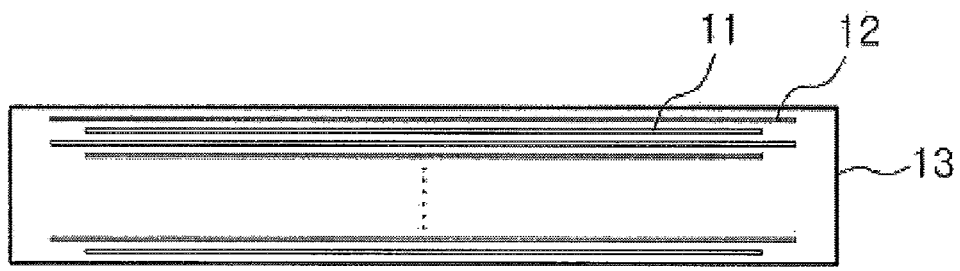
FIG. 1B is a sectional view taken along line A-A' of FIG. 1A.
Figure 3:
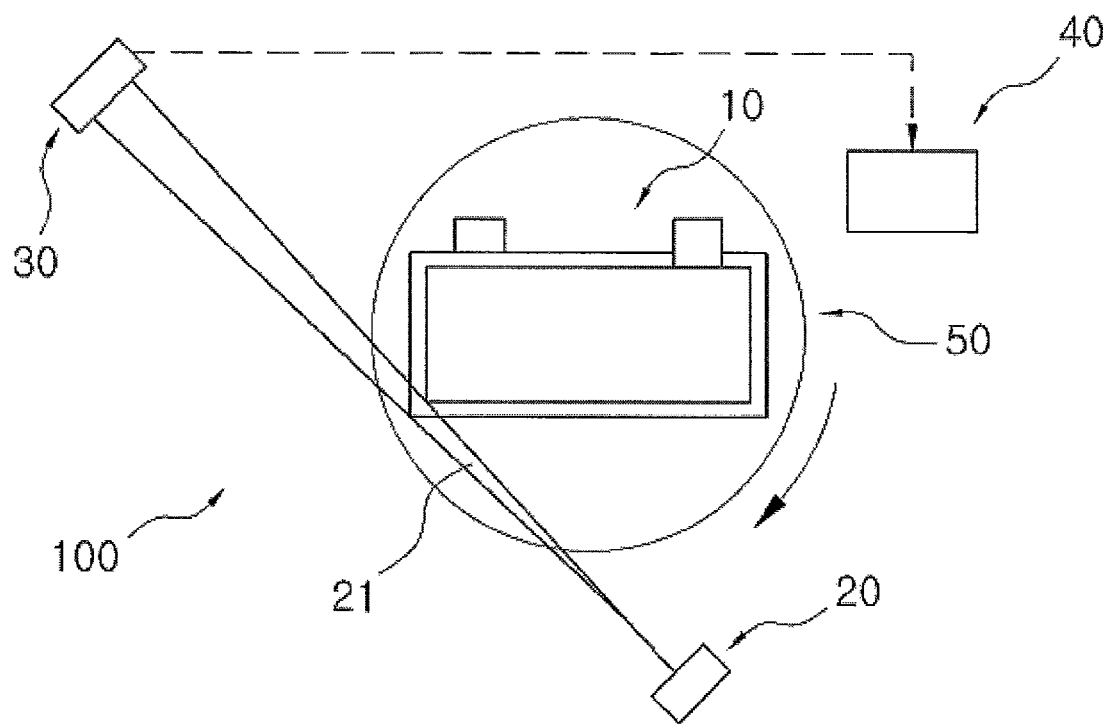
FIG. 3 is a conceptual view showing an apparatus for inspecting the electrodes of a battery according to the present invention.

FIG. 1A is a front view of a battery, and FIG. 1B is a sectional view taken along line A-A' of FIG. 1A. FIG. 3 is a conceptual view showing an apparatus for inspecting the electrodes of a battery according to the present invention, FIG. 4 is a conceptual view showing an inspection method performed by the electrode inspection apparatus according to the present invention, and FIG. 5 is a longitudinal sectional view of portion A of FIG. 4.

Prior to describing embodiments of the present invention, a battery which is the inspection target of the apparatus for inspecting the electrodes of the battery will be described.

FIGS. 1A and 1B show a battery 10 that is based on the lithium-ion polymer battery that is typically used. As shown in the drawings, the battery 10 may be formed such that a plurality of plate-shaped anodes 11 and a plurality of plate-shaped cathodes 12 having larger cross sectional areas than the anodes 11 are alternately stacked. A separator made of a thin resin-based material may be interposed between each anode 11 and each cathode 12. The anodes 11 and cathodes 12 that are stacked may be accommodated in a casing 13 formed of aluminum, polypropylene, and a multi-layer laminate film. An internal space of the casing 13 except for the anodes 11 and the cathodes 12 is filled with an electrolyte (not shown). Further, the respective anodes 11 are connected to anode leads 11a and those anode leads 11a are combined into a single anode lead (not shown), which is exposed to the outside of the casing 13. The respective cathodes 12 are also connected to cathode leads 12a and those cathode leads 12a are combined into a single cathode lead (not shown), which is exposed to the outside of the casing 13.

Figure 4:
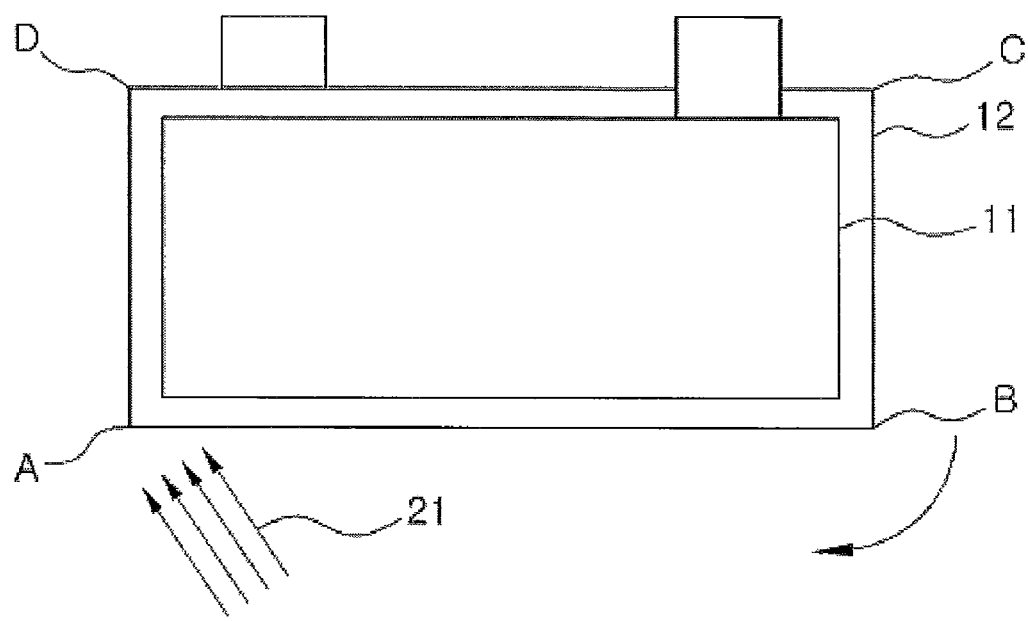
FIG. 4 is a conceptual view showing an inspection method performed by the electrode inspection apparatus according to the present invention.
Figure 5:
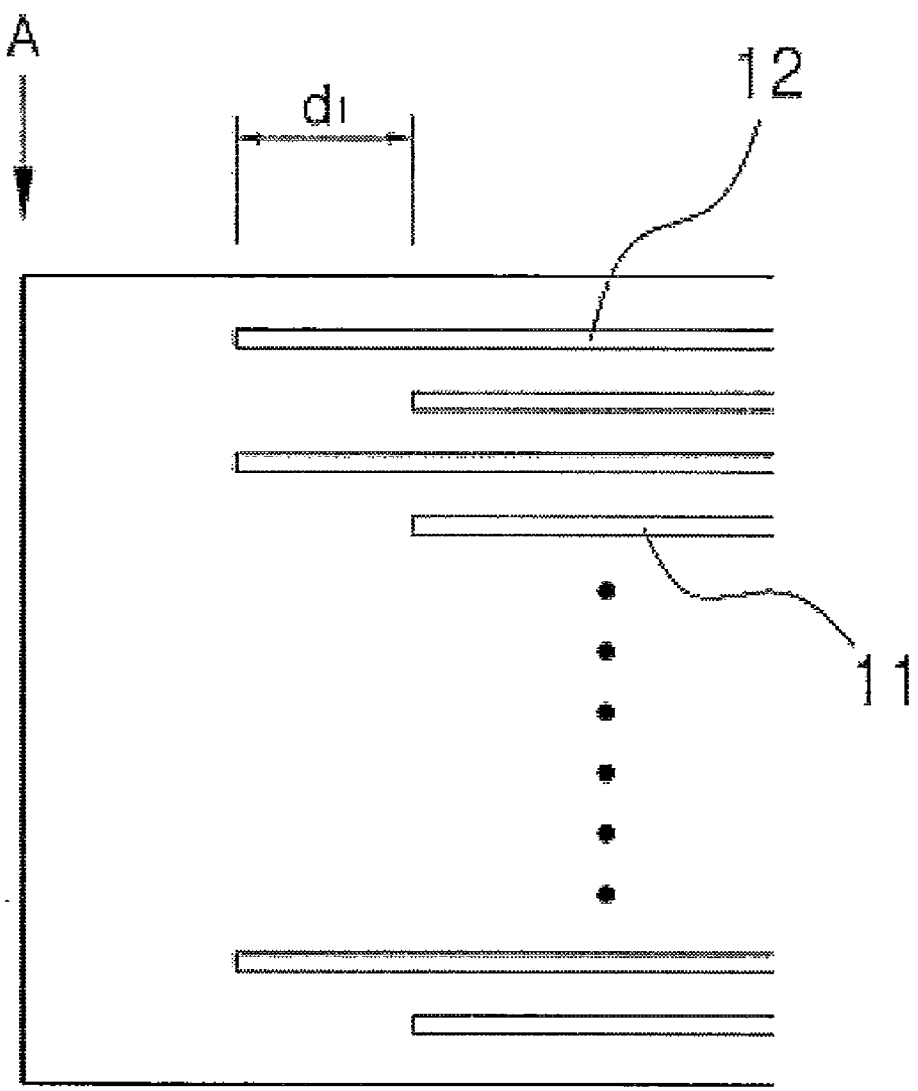
FIG. 5 is a longitudinal sectional view of portion A of FIG. 4.

Referring to FIGS. 3 to 5, the apparatus for inspecting the electrodes of a battery according to the present invention includes a first X-ray source 20 for radiating a first X-ray beam 21, a first detector 30 for detecting an image, created by transmitting the first X-ray beam 21 through the battery 10, in the form of a two-dimensional image, and a control unit 40 for processing the detected image. An inspection plate 50 on which the target battery 10 to be inspected is placed may be installed between the first X-ray source 20 and the first detector 30.

The first X-ray source 20 may be implemented using a typical X-ray tube. As the first X-ray source 20, an X-ray tube having a 0.1 mm focus may be used. The tube voltage of the first X-ray source 20 may be 100 KV, and the tube current thereof may be 0.5 mA.

The first X-ray source 20 functions to radiate the first X-ray beam 21 onto the inspection target battery 10.

The first detector 30 may be used in such a way as to attach a scintillator film, which converts X-rays into visible light, to the surface of a secondary basic semiconductor optical sensor array (Charged Coupled Device: CCD sensor), such as is used in a typical TV camera or the like.

The first detector 30 functions to detect the image, created by transmitting the first X-ray beam 21 through the battery 10, in the form of a two-dimensional image.

The control unit 40 may be implemented as a typical Personal Computer (PC), and functions to read the detected image transmitted from the first detector 30 and to determine whether the stacked surface of the captured battery 10 has deviated from its original location.

The inspection plate 50 may be formed in any shape as long as the shape enables the battery 10 to be placed thereon, and may be provided with a rotating part (not shown) capable of rotating the battery 10 at a preset angle in a horizontal direction under the control of the control unit 40.

Figure 6:
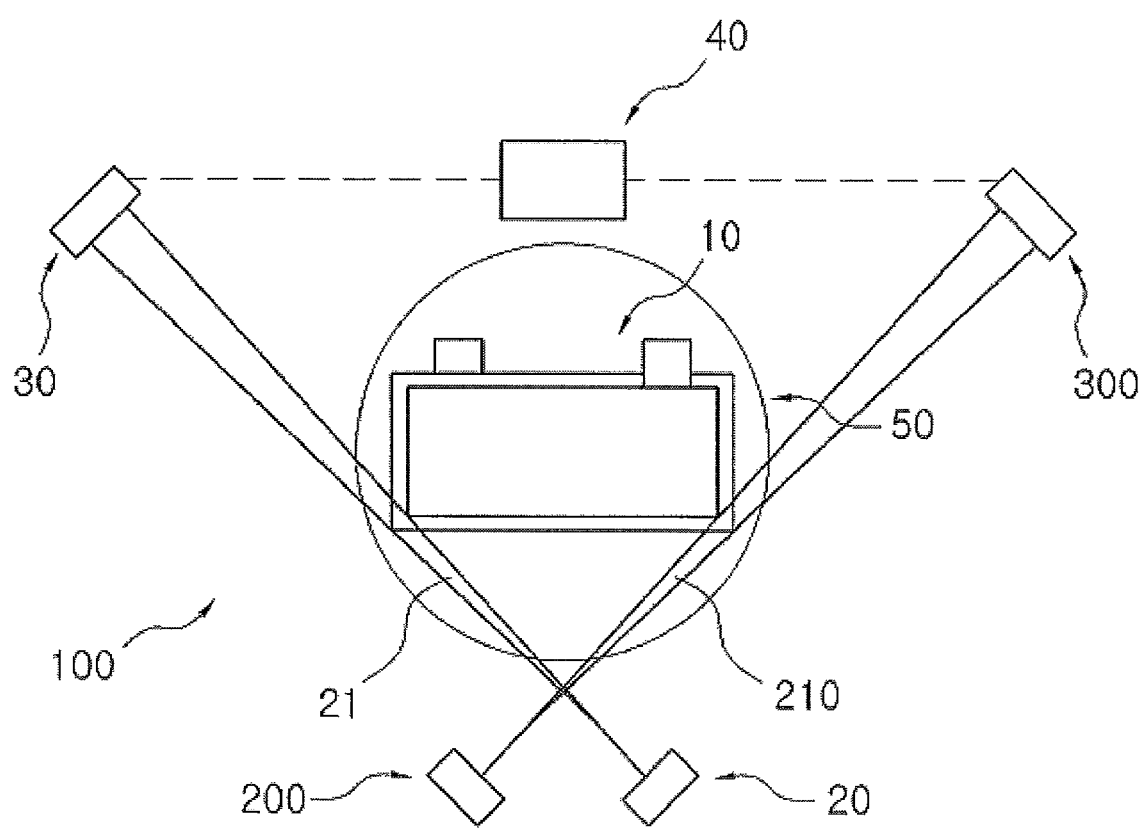
FIG. 6 is a conceptual view showing an apparatus for inspecting the electrodes of a battery according to a second embodiment of the present invention.
Figure 7:
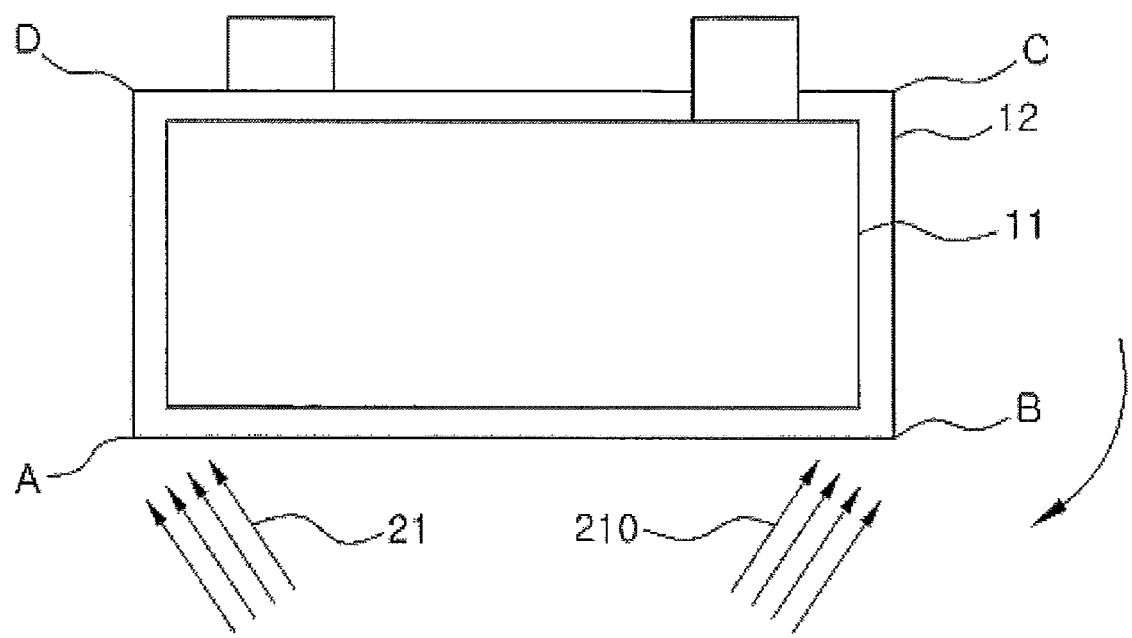
FIG. 7 is a conceptual view showing an inspection method performed by the electrode inspection apparatus according to a second embodiment of the present invention.
Figure 8A:
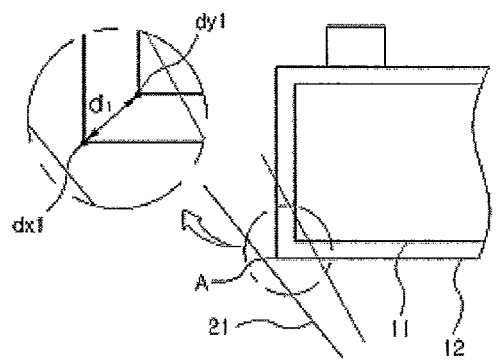
FIGS. 8A to 8D are conceptual views showing a method of inspecting the electrodes of a battery according to the present invention.
Figure 8B:
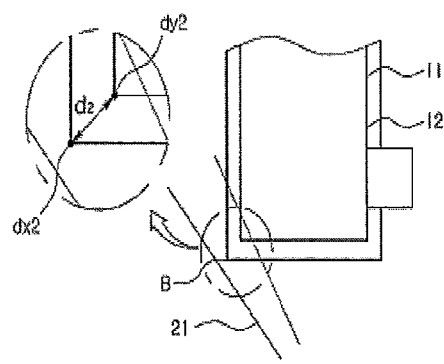
Figure 8C:
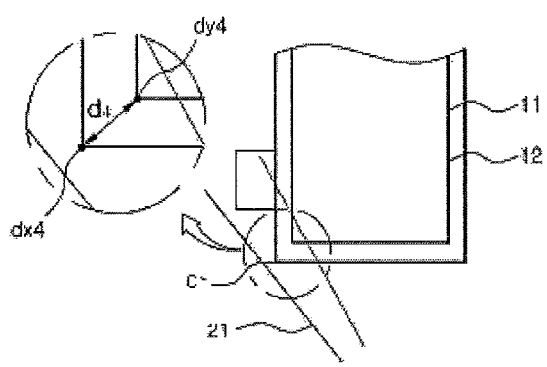
Figure 8D:
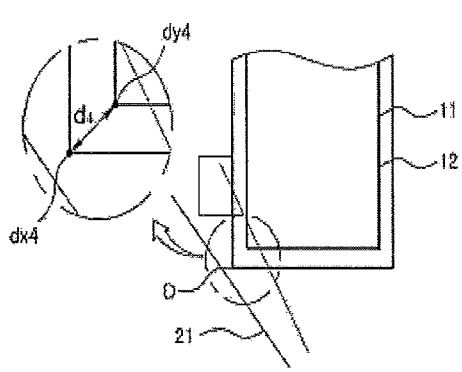

FIG. 6 is a conceptual diagram showing an apparatus for inspecting the electrodes of a battery according to a second embodiment of the present invention, and FIG. 7 is a conceptual diagram showing an inspection method performed by the electrode inspection apparatus according to the embodiment of the present invention.

Referring to FIGS. 6 and 7, the apparatus for inspecting the electrodes of a battery according to the second embodiment of the present invention includes a first X-ray source 20 for radiating a first X-ray beam 21, a first detector 30 for detecting an image, created by transmitting the first X-ray beam 21 through a target battery to be inspected, in the form of a two-dimensional image, a second X-ray source 200 spaced apart from the first X-ray source 20 by a predetermined distance and configured to radiate a second X-ray beam 210, a second detector 300 for detecting an image, created by transmitting the second X-ray beam 210 through the target battery, in the form of a two-dimensional image, and a control unit 40 for processing the images detected by the first and second detectors 30 and 300. An inspection plate 50 on which the target battery 10 to be inspected is placed may be interposed between the first and second X-ray sources 20 and 200 and the first and second detectors 30 and 300. The advantages that can be obtained by the above construction will be described with reference to second and third embodiments of the inspection method performed by the apparatus for inspecting the electrodes of the battery according to the present invention, which will be described later.

Hereinafter, a method of inspecting the electrodes of a battery according to the embodiment of the present invention having the above construction will be described in detail with reference to the drawings.

Figure 9A:
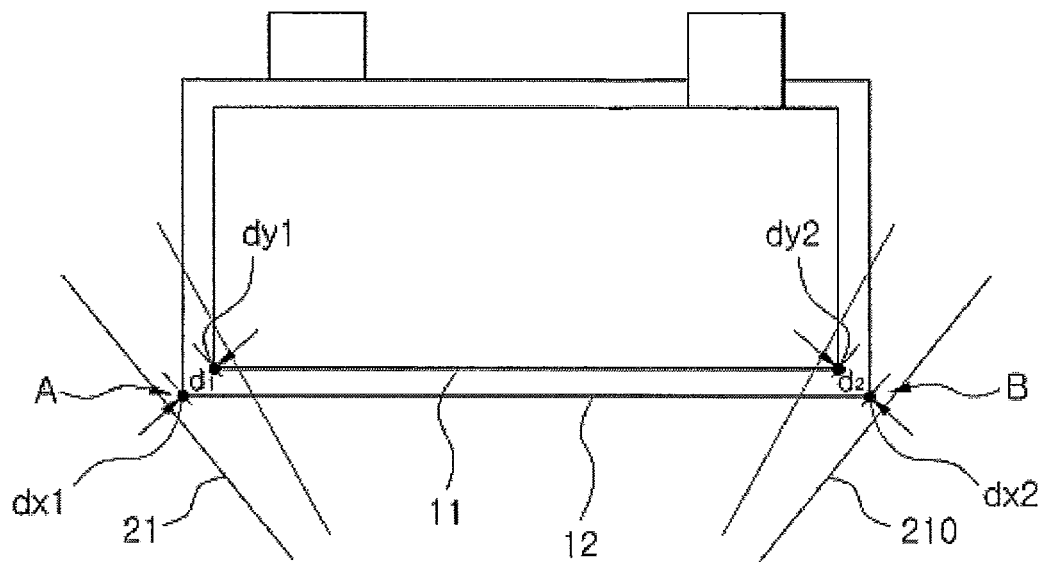
FIGS. 9A and 9B are conceptual views showing the electrode inspection method according to the second embodiment of the present invention.
Figure 9B:
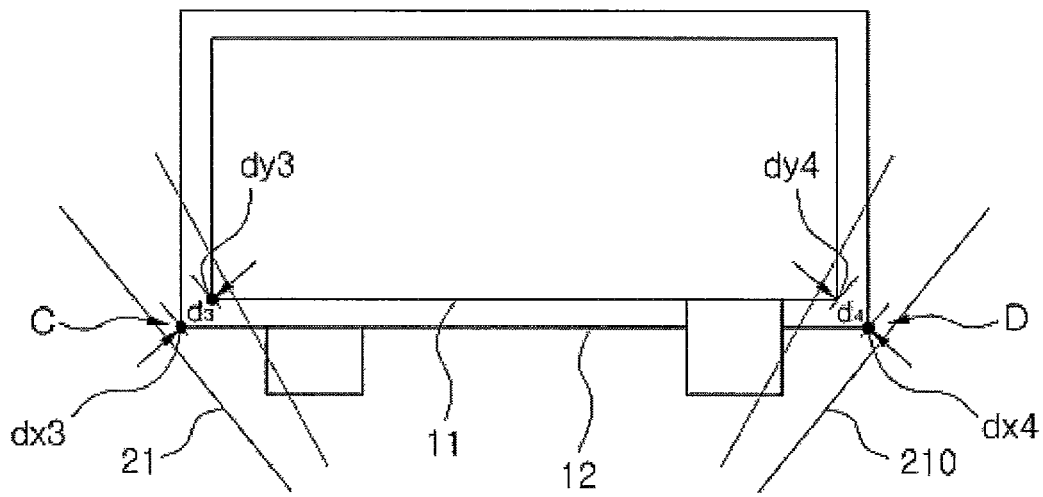
Figure 10A:
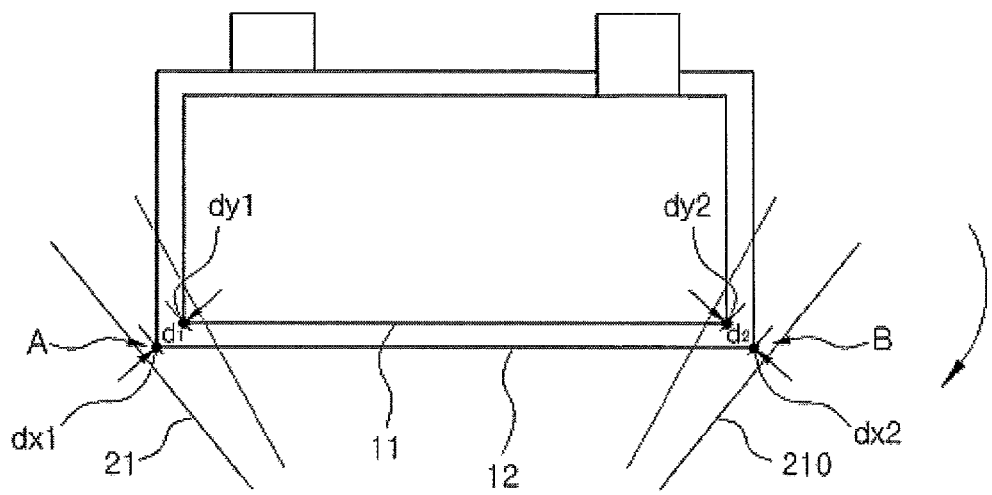
FIGS. 10A and 10B are conceptual views showing the method of inspecting the electrodes of a battery according to a third embodiment of the present invention.
Figure 10B:
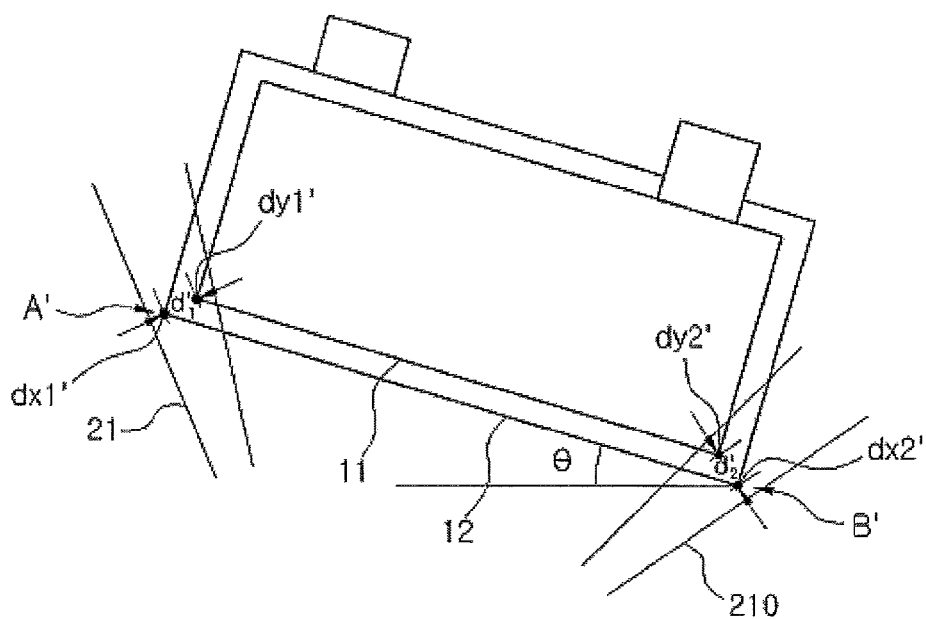
Figure 11:
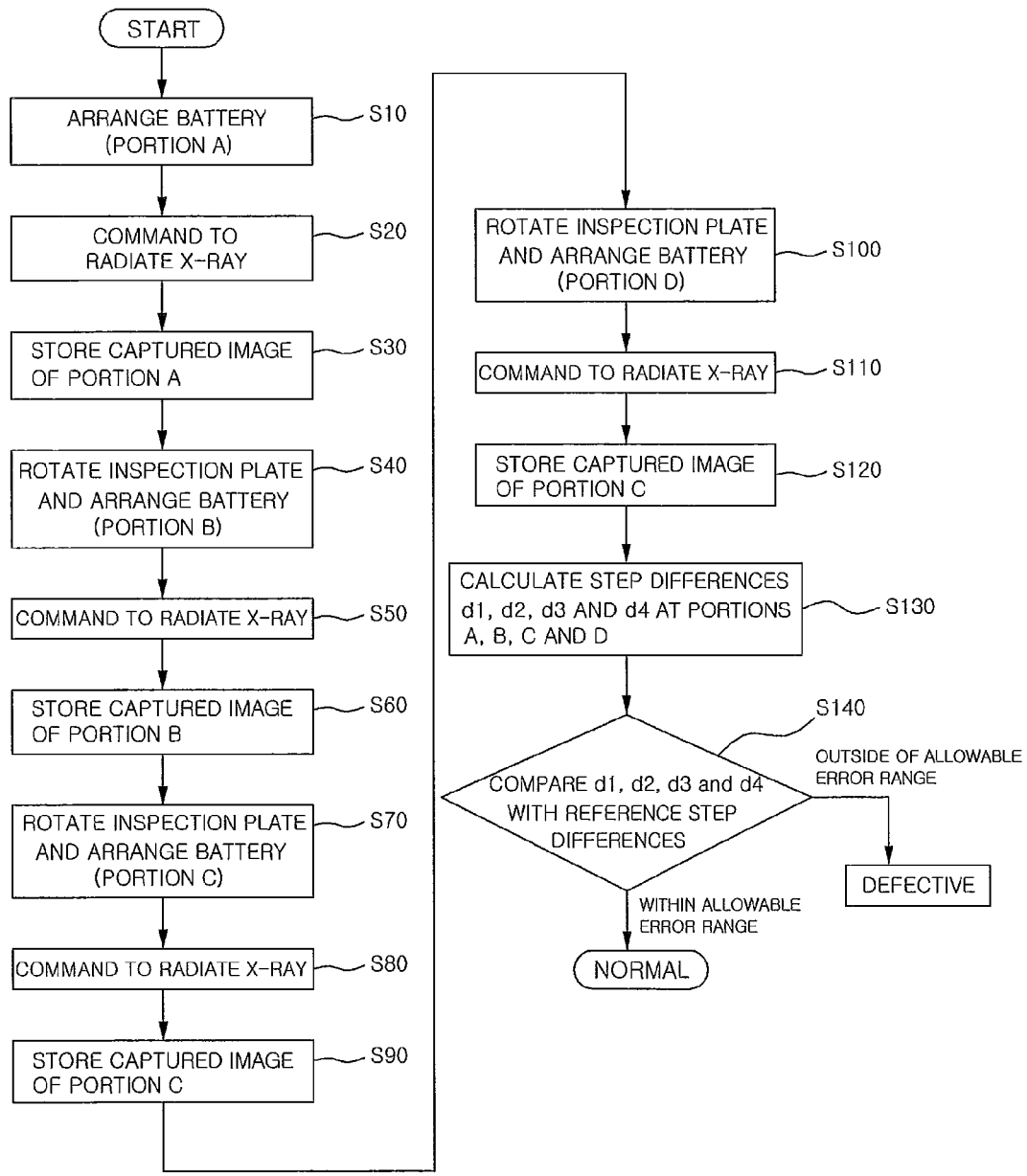
FIG. 11 is a flowchart showing the method of inspecting the electrodes of a battery according to the present invention.
Figure 12:
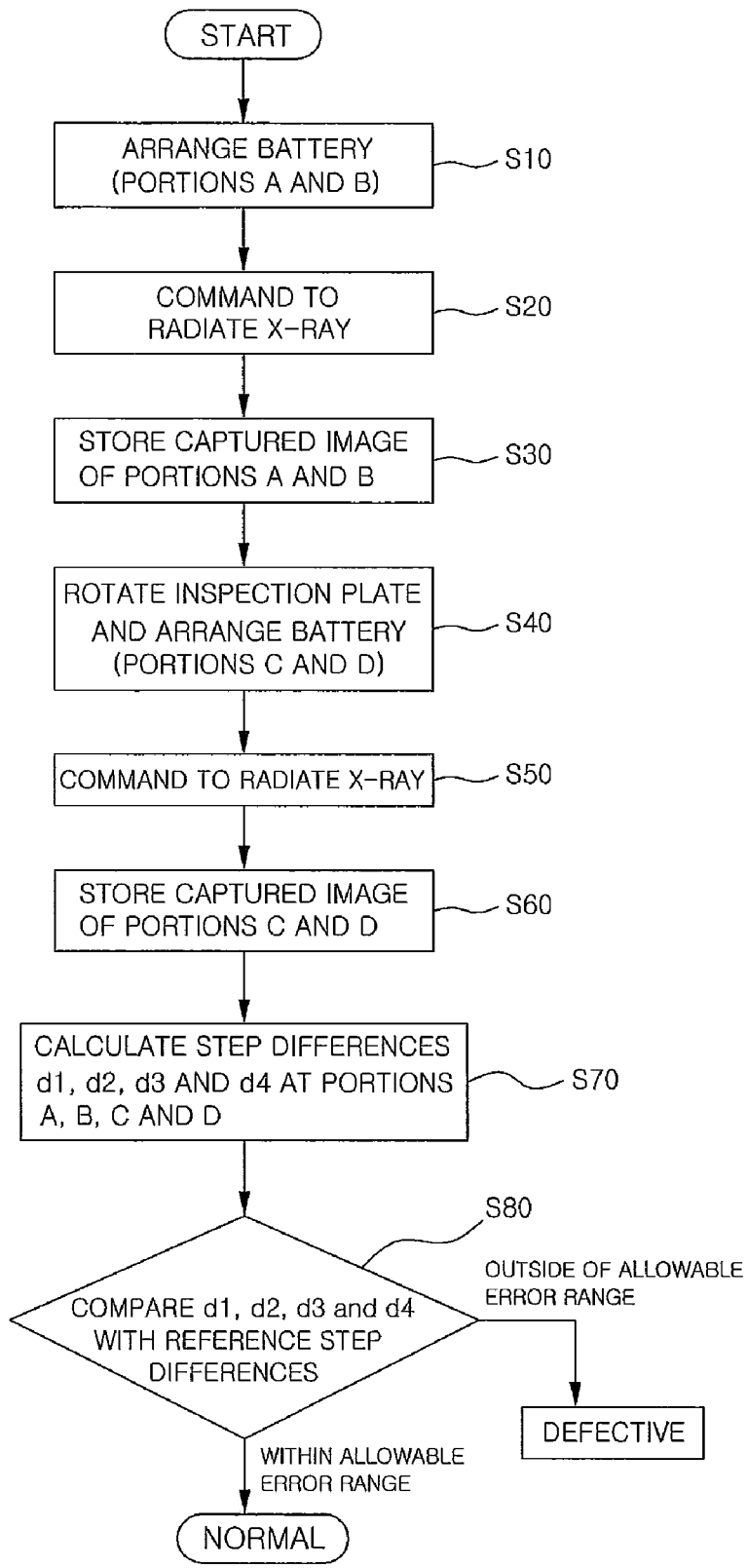
FIG. 12 is a flowchart showing the method of inspecting the electrodes of a battery according to the second embodiment of the present invention.
Figure 13:
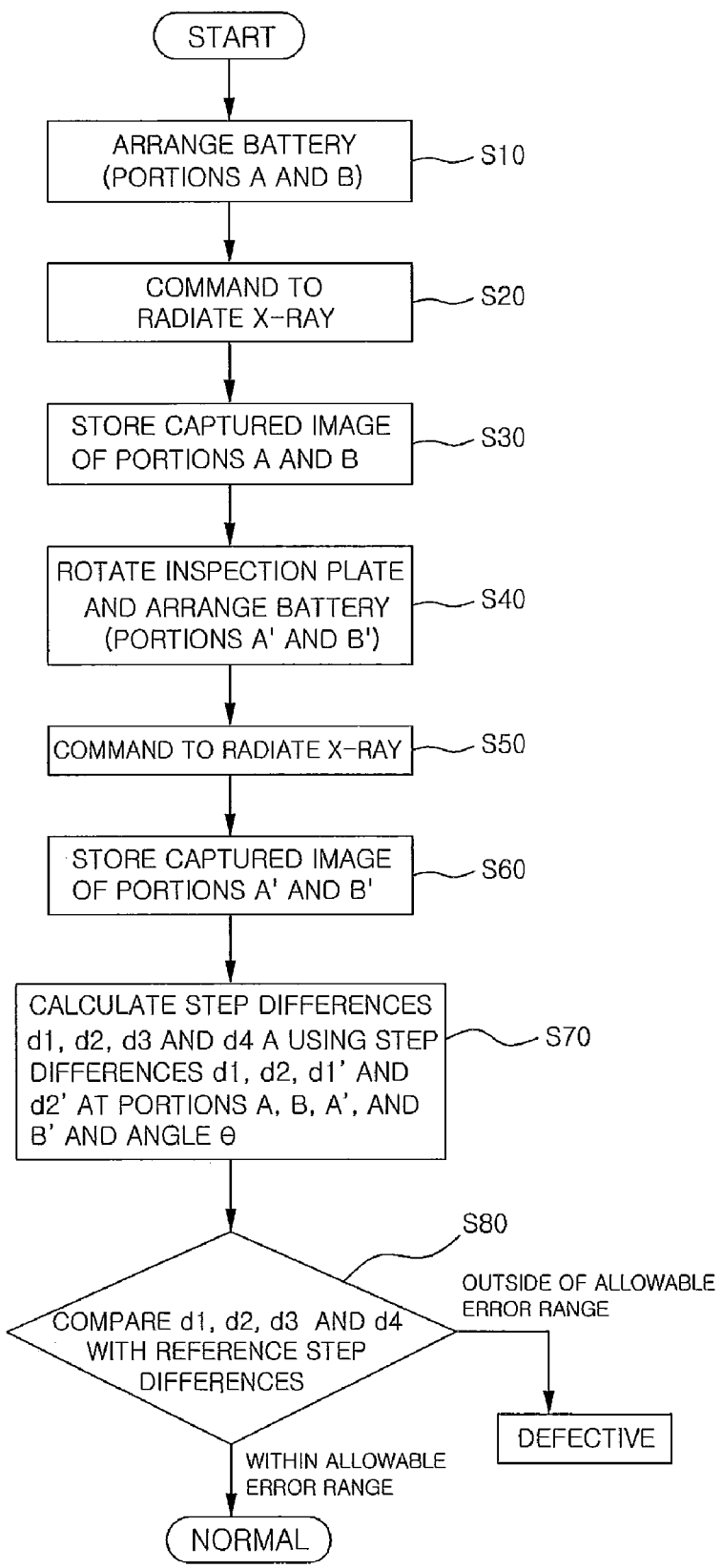
FIG. 13 is a flowchart showing the method of inspecting the electrodes of a battery according to the third embodiment of the present invention.

FIGS. 8A to 8D are conceptual views showing a method of inspecting the electrodes of a battery according to the present invention, FIGS. 9A and 9B are conceptual views showing an electrode inspection method according to a second embodiment of the present invention, and FIGS. 10A and 10B are conceptual views showing a method of inspecting the electrodes of a battery according to a third embodiment of the present invention. FIG. 11 is a flowchart showing the method of inspecting the electrodes of a battery according to the present invention, FIG. 12 is a flowchart showing a method of inspecting the electrodes of a battery according to a second embodiment of the present invention, and FIG. 13 is a flowchart showing a method of inspecting the electrodes of a battery according to a third embodiment of the present invention.

As shown in FIGS. 4 and 7, for convenience of description, a first end (corner) of a first side of a stacked surface of the anode 11 and the cathode 12 of the battery 10 is defined as portion A, a second end of the first side is defined as portion B, a second end of a second side of the stacked surface is defined as portion C, and a first end of the second side is defined as portion D.

First Embodiment of the Inspection Method

Referring to FIGS. 8A to 8D and 11, at step S10, the battery 10 is determined to be arranged on the top of the inspection plate 50, and is then arranged thereon. In this case, the arrangement location of the battery 10 is determined such that the portion A of the battery 10 is parallel with the stacked surface of each anode 11 and each cathode 12 of the battery 10 so as to inspect the portion A of the battery 10. However, the battery 10 may be located so that the X-ray beam is radiated onto the portion A of the battery at a predetermined angle of inclination in a direction horizontal to the ground surface. The process proceeds to step S20 at the same time that the control unit 40 determines that the battery 10 has been placed as described above.

At step S20, the control unit 40 commands the first X-ray source 20 to radiate the first X-ray beam 21. When the first X-ray beam 21 is radiated from the first X-ray source 20, the first X-ray beam 21 is radiated onto the battery 10, and the first X-ray beam 21 having transmitted through the battery 10 is captured by the first detector 30. In this case, the first X-ray beam 21 may be radiated onto the portion A of the battery 10 so that it is inclined at a predetermined angle.

At step S30, a transmission image A captured by the first detector 30 is stored and retained in the control unit 40.

At step S40, after the inspection plate 50 has been rotated clockwise at an angle of 90 degrees by the control unit 40, the battery 10 may be located such that the X-ray beam is radiated onto a portion B of the battery 10 at a predetermined angle of inclination in a direction horizontal to the ground surface. The process proceeds to step S50 at the same time that the control unit 40 determines that the battery 10 has been placed as described above.

At step S50, the control unit 40 commands the first X-ray source 20 to radiate the first X-ray beam 21. When the first X-ray beam 21 is radiated from the first X-ray source 20, the first X-ray beam 21 is radiated onto the battery 10, and the first X-ray beam 21 having transmitted through the battery 10 is captured by the first detector 30. In this case, the first X-ray beam 21 may be radiated onto the portion B of the battery 10 at a predetermined angle of inclination.

At step S60, a transmission image B captured by the first detector 30 is stored and retained in the control unit 40.

At step S70, after the inspection plate 50 has been rotated clockwise at an angle of 90 degrees by the control unit 40, the battery 10 may be located such that the X-ray beam is radiated onto portion C of the battery 10 at a predetermined angle of inclination in a direction horizontal to the ground surface. The process proceeds to step S80 at the same time that the control unit 40 determines that the battery 10 has been placed as described above.

At step S80, the control unit 40 commands the first X-ray source 20 to radiate the first X-ray beam 21. When the first X-ray beam 21 is radiated from the first X-ray source 20, the first X-ray beam 21 is radiated onto the battery 10, and the first X-ray beam 21 having transmitted through the battery 10 is captured by the first detector 30. In this case, the first X-ray beam 21 may be radiated onto the portion C of the battery 10 at a predetermined angle of inclination.

At step S90, a transmission image C captured by the first detector 30 is stored and retained in the control unit 40.

At step S100, after the inspection plate 50 has been rotated clockwise at an angle of 90 degrees by the control unit 40, the battery 10 may be located such that the X-ray beam is radiated onto portion D of the battery 10 at a predetermined angle of inclination in a direction horizontal to the ground surface. The process proceeds to step S110 at the same time that the control unit 40 determines that the battery 10 has been placed as described above.

At step S110, the control unit 40 commands the first X-ray source 20 to radiate the first X-ray beam 21. When the first X-ray beam 21 is radiated from the first X-ray source 20, the first X-ray beam 21 is radiated onto the battery 10, and the first X-ray beam 21 having transmitted through the battery 10 is captured by the first detector 30. In this case, the first X-ray beam 21 may be radiated onto the portion D of the battery 10 at a predetermined angle of inclination.

At step S120, a transmission image D captured by the first detector 30 is stored and retained in the control unit 40.

At step S130, the transmission images A, B, C, and D stored in the control unit 40 are respectively read, and step differences d1, d2, d3, and d4 between the anode 11 and the cathode 12 of the battery are calculated. Here, the step difference d1 may be defined as the difference (dx1−dy1) between the determined coordinate value dx1 of the cathode 12 and the determined coordinate value dy1 of the anode 11.

At step S140, the control unit 40 compares the calculated step differences d1, d2, d3, and d4 with prestored reference step differences, respectively, and then determines whether the stacked surface of the battery has deviated from its original location. If resulting comparison values fall within an allowable range of error, the control unit 40 determines that the stacked state of the electrodes of the battery is normal, whereas if they fall outside of the allowable range of error, the control unit 40 determines that the stacked state of the electrodes of the battery is defective, and thereafter terminates the inspections.

The inspection method in the above-described first embodiment radiates the first X-ray beam 21 onto the portions A, B, C, and D of the battery 10, that is, corners of the battery 10 in a diagonal direction, so that the distance the first X-ray beam 21 is transmitted is shortened, thus enabling accurate inspections to be conducted. This is due to the fact that when the distance the first X-ray beam 21 is transmitted is equal to or greater than a predetermined distance as described above, it is difficult to obtain accurate images due to the scattering of frequencies.

Second Embodiment of the Inspection Method

Referring to FIGS. 9A and 9B and 12, the method of inspecting the electrodes of a battery according to a second embodiment of the present invention is described as follows.

At step S10, the battery 10 is determined to be arranged on the top of the inspection plate 50, and is then arranged thereon. In this case, the arrangement location of the battery 10 is determined such that the portions A and B of the battery 10 are parallel with the stacked surface of each anode 11 and each cathode 12 of the battery 10 so as to inspect the portions A and B of the battery 10. However, the portion A of the battery 10 may be located so that the X-ray beam is radiated by the first X-ray source 20 onto the portion A of the battery at a predetermined angle of inclination in a direction horizontal to the ground surface. Further, the portion B of the battery 10 may be located so that the X-ray beam is radiated by the second X-ray source 200 onto the portion B of the battery at a predetermined angle of inclination in a direction horizontal to the ground surface. The process proceeds to step S20 at the same time that the control unit 40 determines that the battery 10 has been placed as described above.

At step S20, the control unit 40 commands the first and second X-ray sources 20 and 200 to radiate first and second X-ray beams 21 and 210. When the first and second X-ray beams 21 and 210 are radiated from the first and second X-ray sources 20 and 200, the first and second X-ray beams 21 and 210 are radiated onto the battery 10, and the first and second X-ray beams 21 and 210 having transmitted through the battery 10 are captured by the first and second detectors 30 and 300. In this case, the first X-ray beam 21 may be radiated onto the portion A of the battery 10 at a predetermined angle of inclination. The second X-ray beam 210 may be radiated onto the portion B of the battery 10 at a predetermined angle of inclination.

At step S30, a transmission image A captured by the first detector 30 and a transmission image B captured by the second detector 300 are stored and retained in the control unit 40.

At step S40, after the inspection plate 50 has been rotated clockwise by 180 degrees by the control unit 40, the battery 10 may be located such that the X-ray beams are radiated onto portions C and D of the battery 10 at a predetermined angle of inclination in a direction horizontal to the ground surface. The process proceeds to step S50 at the same time that the control unit 40 determines that the battery 10 has been placed as described above.

At step S50, the control unit 40 commands the first and second X-ray sources 20 and 200 to radiate the first and second X-ray beams 21 and 210. When the first and second X-ray beams 21 and 210 are radiated from the first and second X-ray sources 20 and 200, the first and second X-ray beams 21 and 210 are radiated onto the battery 10, and the first and second X-ray beams 21 and 210 having transmitted through the battery 10 are respectively captured by the first and second detectors 30 and 300. In this case, the first X-ray beam 21 may be radiated onto the portion C of the battery 10 at a predetermined angle of inclination, and the second X-ray beam 210 may be radiated onto the portion D of the battery 10 at a predetermined angle of inclination.

At step S60, a transmission image C captured by the first detector 30 and a transmission image D captured by the second detector 300 are stored and retained in the control unit 40.

At step S70, the transmission images A, B, C, and D stored in the control unit 40 are respectively read therefrom, and step differences d1, d2, d3, and d4 between the anode 11 and the cathode 12 are calculated. In this case, the step difference d1 may be defined as the difference (dx1−dy1) between the determined coordinate value dx1 of the cathode 12 and the determined coordinate value dy1 of the anode 11.

At step S80, the control unit 40 compares the calculated step differences d1, d2, d3, and d4 with prestored reference step differences, respectively, and then determines whether the stacked surface of the battery has deviated from its original location. If resulting comparison values fall within an allowable range of error, the control unit 40 determines that the stacked state of the electrodes of the battery is normal, whereas if they fall outside of the allowable range of error, the control unit 40 determines that the stacked state of the electrodes is defective, and terminates the inspections.

Compared to the above-described inspection method in the first embodiment, the above-described inspection method in the second embodiment moves the inspection plate 50 only once without moving the inspection plate 50 three times for the locations at which the battery will be captured, so that the time required for the inspections can be reduced by half, and thus prompt inspections can be conducted.

Third Embodiment of the Inspection Method

Referring to FIGS. 9A and 9B and 13, the method of inspecting the electrodes of a battery according to a third embodiment of the present invention is described as follows.

At step S10, the battery 10 is determined to be arranged on the top of the inspection plate 50, and is then arranged thereon. In this case, the arrangement location of the battery 10 is determined such that the portions A and B of the battery 10 are parallel with the stacked surface of each anode 11 and each cathode 12 of the battery 10 so as to inspect the portions A and B of the battery 10. However, the portion A of the battery 10 may be located so that the X-ray beam is radiated by the first X-ray source 20 onto the portion A of the battery 10 at a predetermined angle of inclination in a direction horizontal to the ground surface. Further, the portion B of the battery 10 may be located so that the X-ray beam is radiated by the second X-ray source 200 onto the portion B of the battery at a predetermined angle of inclination in a direction horizontal to the ground surface. The process proceeds to step S20 at the same time that the control unit 40 determines that the battery 10 has been placed as described above.

At step S20, the control unit 40 commands the first and second X-ray sources 20 and 200 to radiate first and second X-ray beams 21 and 210. When the first and second X-ray beams 21 and 210 are radiated from the first and second X-ray sources 20 and 200, the first and second X-ray beams 21 and 210 are radiated onto the battery 10, and the first and second X-ray beams 21 and 210 having transmitted through the battery 10 are captured by the first and second detectors 30 and 300. In this case, the first X-ray beam 21 may be radiated onto the portion A of the battery 10 at a predetermined angle of inclination. The second X-ray beam 210 may be radiated onto the portion B of the battery 10 at a predetermined angle of inclination.

At step S30, a transmission image A captured by the first detector 30 and a transmission image B captured by the second detector 300 are stored and retained in the control unit 40.

At step S40, after the inspection plate 50 has been rotated clockwise at an angle of less than 90 degrees by the control unit 40, the battery 10 may be located such that the X-ray beams are radiated onto portions A' and B' of the battery 10 at a predetermined angle of inclination in a direction horizontal to the ground surface. The process proceeds to step S50 at the same time that the control unit 40 determines that the battery 10 has been placed as described above.

At step S50, the control unit 40 commands the first and second X-ray sources 20 and 200 to radiate the first and second X-ray beams 21 and 210. When the first and second X-ray beams 21 and 210 are radiated from the first and second X-ray sources 20 and 200, the first and second X-ray beams 21 and 210 are radiated onto the battery 10, and the first and second X-ray beams 21 and 210 having transmitted through the battery 10 are respectively captured by the first and second detectors 30 and 300. In this case, the first X-ray beam 21 may be radiated onto the portion A' of the battery 10 at a predetermined angle of inclination, and the second X-ray beam 210 may be radiated onto the portion B' of the battery 10 at a predetermined angle of inclination.

At step S60, a transmission image A' captured by the first detector 30 and a transmission image B' captured by the second detector 300 are stored and retained in the control unit 40.

At step S70, the transmission images A, A', B, and B' stored in the control unit 40 are respectively read therefrom, and step differences d1, d1', d2, and d2' between the anode 11 and the cathode 12 are calculated. In this case, the step difference $d_1$ may be defined as the difference (dx1−dy1) between the determined coordinate value dx1 of the cathode 12 and the determined coordinate value dy1 of the anode 11.

At step S80, the control unit 40 calculates the step differences d1, d2, d3, and d4 using both the calculated step differences d1, d1', d2, and d2' and the rotation angle θ at step S40, compares the step differences d1, d2, d3, and d4 with prestored reference step differences, respectively, and then determines whether the stacked surface of the battery has deviated from its original location. If the resulting comparison values fall within an allowable range of error, the control unit 40 determines that the stacked state of the electrodes is normal, whereas if they fall outside of the allowable range of error, the control unit 40 determines that the stacked state of the electrodes is defective, and then terminates the inspections.

Compared to the above-described inspection method in the second embodiment, the inspection method in the third embodiment can reduce the distance of movement even if the second and third embodiments are identical in that the inspection plate 50 is moved once for the locations at which the battery will be captured, so that the time required for the inspections can be reduced, and thus prompt inspections can be conducted.

Fourth Embodiment of the Inspection Method

The inspection methods in the above-described first to third embodiments determine the normality or defectiveness of the stacked state of cell electrodes by calculating diagonal distances between the corners of each anode 11 and the corners of each cathode 12. However, at the time when batteries are designed, lateral and longitudinal step differences between the anode 11 and the cathode 12, that is, the distance between the lateral side of the anode 11 and the lateral side of the cathode 12 and the distance between the longitudinal side of the anode 11 and the longitudinal side of the cathode 12, are designed, and are applied to specifications.

Therefore, each battery is designed and applied depending on diagonal specifications based on inspection angles when the battery is inspected using the above inspection methods in the above-described first to third embodiments. As a result, there is a problem in that the time and expenses required for such an inspection are greatly increased.

In order to overcome this problem, the present invention is intended to propose a method of calculating lateral and longitudinal distances using diagonal lengths at two different angles by using the inspection method in the third embodiment.

In the calculation method which will be described later, a first corner A of one side of the battery 10 will be described as an example, but it is apparent that this method can be applied to any corner of the battery 10.

Figure 14:
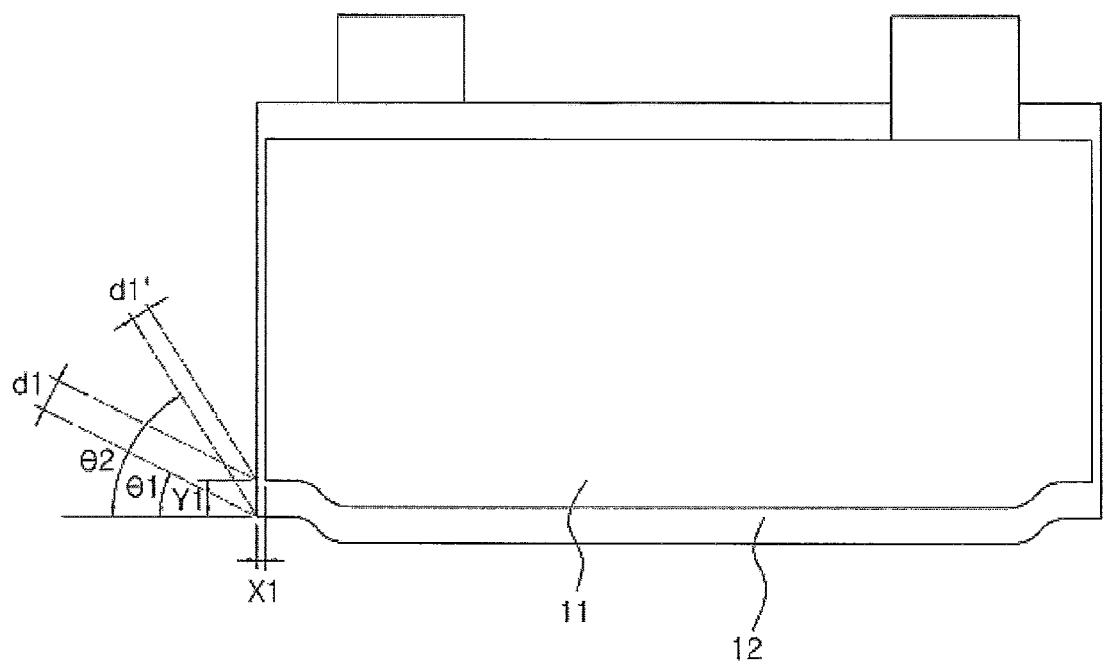
FIG. 14 is a conceptual view showing a method of inspecting the electrodes of a battery according to a fourth embodiment of the present invention.

Referring to FIG. 14, the distance between an anode corner dy1 and a cathode corner dx1 at the first corner A of the first side of the battery 10, measured by the X-ray source 20 in the inspection method according to the third embodiment, is defined as d1. An angle formed between the lateral side of the cathode 12 and the first X-ray source 20 at the time of measuring d1 is defined as θ1.

Further, after the battery 10 has been rotated at a predetermined angle, the distance between an anode corner dy1' and a cathode corner dx1' at the first corner A' of the first side of the battery 10, which are measured by the X-ray source 20 and have changed due to the change in the angle of the battery 10, is defined as d1'. An angle formed between the lateral side of the cathode 12 and the first X-ray source 20 at the time of measuring d1' is defined as θ2.

In this case, the distance X1 between the lateral side of the anode 11 and the lateral side of the cathode 12 at the first corner A of the first side of the battery 10 and the distance Y1 between the longitudinal side of the anode 11 and the longitudinal side of the cathode 12 at the first corner A of the first side of the battery 10 are calculated by the following Equations. In order to calculate the following Equations, the assumption that the lateral sides of the anode 11 and the cathode 12 must be parallel with each other and θ1 and θ2 must be greater than 0 degrees and less than 90 degrees is required.

$$X1 = \frac{1}{\tan(\theta 2) - \tan(\theta 1)}\left(\frac{d1'}{\cos(\theta 2)} - \frac{d1}{\cos(\theta 1)}\right)$$

$$Y1 = \frac{-\tan(\theta 1)}{\tan(\theta 2) - \tan(\theta 1)}\left(\frac{d1'}{\cos(\theta 2)} - \frac{d1}{\cos(\theta 1)}\right) + \frac{d1}{\cos(\theta 1)}$$

Through the above method, the present invention can obtain specifications of the distance X1 between the lateral sides of the anode 11 and the cathode 12 and the distance Y1 between the longitudinal sides of the anode 11 and the cathode 12, which are required for the design of batteries while determining the normality or defectiveness of the stacked state of the cell electrodes of the battery 10, thus obtaining an advantage of reducing the time and expenses required to manufacture batteries.

As described above, the present invention provides an apparatus and method for inspecting the electrodes of a battery, having the above construction, which is advantageous in that the arrangement state of cell electrodes is measured by transmitting X-rays through corners of the battery, thus improving the reliability of inspections by more precisely measuring the arrangement state of the cell electrodes, and reducing the time and expenses required to conduct inspections.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for inspecting electrodes of a battery, the apparatus radiating X-ray beams onto a battery in which a plurality of plate-shaped anodes and a plurality of plate-shaped cathodes are alternately stacked and inspecting an arrangement state of the anodes and the cathodes, the apparatus comprising:
a first X-ray source part for radiating a first X-ray beam onto the battery;
a first detector for detecting the first X-ray beam having transmitted through the battery; and
a control unit for receiving an image of the battery output from the first detector, calculating a step difference between each anode and each cathode, and then inspecting an arrangement state of the anode and the cathode,
wherein the first X-ray source part radiates the first X-ray beam in a direction parallel with a stacked surface of the anode and the cathode of the battery so that the first X-ray beam is radiated at a predetermined angle of inclination in a direction horizontal to a ground surface.

2. The apparatus according to claim 1, further comprising an inspection plate configured to allow the battery to be placed thereon and to be rotated in a horizontal direction.

3. The apparatus according to claim 2, further comprising:
a second X-ray source part spaced apart from the first X-ray source part by a predetermined distance and configured to radiate a second X-ray beam onto the battery; and
a second detector for detecting the second X-ray beam having transmitted through the battery,
wherein both corners of a first side or a second side of the stacked surface of the anode and the cathode of the battery are simultaneously captured by the first X-ray source part and the second X-ray source part, and
wherein an image of the battery output from the second detector enables a step difference between the anode and the cathode to be calculated by the control unit, thus enabling the arrangement state of the anode and the cathode to be inspected.

4. A method of inspecting electrodes of a battery using the apparatus for inspecting the electrodes of the battery according to claim 2, wherein the first X-ray source part rotates the battery by rotating the inspection plate, and sequentially radiates the X-ray beams onto both corners (A and B) of a first side and both corners (C and D) of a second side of the stacked surface of the anode and the cathode of the battery, four times.

5. A method of inspecting electrodes of a battery using the apparatus for inspecting the electrodes of the battery according to claim 3, wherein the first X-ray source part radiates the X-ray beam onto a first corner (A) of the first side of the stacked surface of the anode and the cathode of the battery while the second X-ray source part radiates the X-ray beam onto a second corner (B) of the first side of the stacked surface of the anode and the cathode of the battery, the inspection plate is rotated at an angle of 180 degrees, and then the first X-ray source part radiates the X-ray beam onto a second corner (C) of the second side of the stacked surface of the anode and the cathode of the battery while the second X-ray source part radiates the X-ray beam onto a first corner (D) of the second side of the stacked surface of the anode and the cathode of the battery.

6. A method of inspecting electrodes of a battery using the apparatus for inspecting the electrodes of the battery according to claim 3, wherein the first X-ray source part radiates the X-ray beam onto a first corner (A) of the first side of the stacked surface of the anode and the cathode of the battery while the second X-ray source part radiates the X-ray beam onto a second corner (B) of the first side of the stacked surface of the anode and the cathode of the battery, the inspection plate is rotated at an angle of less than 90 degrees to rotate the battery at a predetermined angle, and then the first X-ray source part radiates the X-ray beam onto a first corner (A') of the first side of the stacked surface, an angle of which has changed while the second X-ray source part radiates the X-ray beam onto a second corner (B') of the first side of the stacked surface, an angle of which has changed.

7. The method according to claim 6, wherein:
if a distance between an anode corner (dy1) and a cathode corner (dx1) at the first corner (A) of the first side of the battery, which have been measured by the first X-ray source part is defined as d1;

an angle formed between a lateral side of the cathode and the first X-ray source part when $d_1$ is measured is defined as $\theta 1$;

a distance between an anode corner (dy1') and a cathode corner (dx1') at the first corner (A') of the first side of the battery, which have been measured by the first X-ray source part and have changed due to a change in the angle of the battery after the battery had been rotated at the predetermined angle, is defined as d1'; and an angle formed between the lateral side of the cathode and the first X-ray source part when the distance (d1') is measured is defined as $\theta 2$, a distance (X1) between a lateral side of the anode and the lateral side of the cathode at the first corner (A) of the first side of the battery and a distance (Y1) between a longitudinal side of the anode and a longitudinal side of the cathode at the first corner (A) of the first side of the battery are calculated by the following equations:

$$X1 = \frac{1}{\tan(\theta 2) - \tan(\theta 1)} \left( \frac{d1'}{\cos(\theta 2)} - \frac{d1}{\cos(\theta 1)} \right)$$

$$Y1 = \frac{-\tan(\theta 1)}{\tan(\theta 2) - \tan(\theta 1)} \left( \frac{d1'}{\cos(\theta 2)} - \frac{d1}{\cos(\theta 1)} \right) + \frac{d1}{\cos(\theta 1)}.$$

* * * * *